United States Patent
Rocabayera Bonvila et al.

(10) Patent No.: US 8,933,122 B2
(45) Date of Patent: Jan. 13, 2015

(54) USE OF CATIONIC SURFACTANTS AS SPORICIDAL AGENTS

(75) Inventors: Xavier Rocabayera Bonvila, Palau-Solità (ES); Sergi Figueras Roca, Barcelona (ES); Roger Segret Pons, Barcelona (ES); Eva Piera Eroles, Barcelona (ES)

(73) Assignee: Laboratorios Miret, S.A., Les Fonts de Terrassa (Barcelona) (ES)

( * ) Notice: Subject to any disclaimer, the term of this patent is extended or adjusted under 35 U.S.C. 154(b) by 525 days.

(21) Appl. No.: 13/000,383

(22) PCT Filed: Jun. 30, 2009

(86) PCT No.: PCT/EP2009/058197
§ 371 (c)(1),
(2), (4) Date: Feb. 21, 2011

(87) PCT Pub. No.: WO2010/000744
PCT Pub. Date: Jan. 7, 2010

(65) Prior Publication Data
US 2011/0144203 A1 Jun. 16, 2011

Related U.S. Application Data

(60) Provisional application No. 61/093,787, filed on Sep. 3, 2008.

(30) Foreign Application Priority Data

Jul. 2, 2008 (EP) .................................... 08382025

(51) Int. Cl.
| | | |
|---|---|---|
| *A61L 101/36* | (2006.01) | |
| *A61L 2/16* | (2006.01) | |
| *A01N 37/44* | (2006.01) | |
| *A01N 37/46* | (2006.01) | |
| *A01P 1/00* | (2006.01) | |
| *A01P 3/00* | (2006.01) | |
| *A01N 47/44* | (2006.01) | |
| *A01N 43/50* | (2006.01) | |
| *A23L 3/3463* | (2006.01) | |
| *A23L 3/3499* | (2006.01) | |
| *A23L 3/3517* | (2006.01) | |
| *A23L 3/3526* | (2006.01) | |
| *C11D 1/10* | (2006.01) | |
| *C11D 3/48* | (2006.01) | |
| *A61L 2/18* | (2006.01) | |

(52) U.S. Cl.
CPC ................ *A01N 47/44* (2013.01); *A01N 37/46* (2013.01); *A01N 43/50* (2013.01); *A23L 3/3463* (2013.01); *A23L 3/3499* (2013.01); *A23L 3/3517* (2013.01); *A23L 3/3526* (2013.01); *C11D 1/10* (2013.01); *C11D 3/48* (2013.01); *A61L 2/18* (2013.01)
USPC ............ 514/551; 514/552; 514/613; 514/634

(58) Field of Classification Search
CPC ....... A61L 2/16; A23L 3/3517; A23L 3/3526; A01N 37/44; A01N 37/46
USPC .................................. 514/551, 552, 613, 634
See application file for complete search history.

(56) References Cited

U.S. PATENT DOCUMENTS

2004/0175350 A1* 9/2004 Urgell Beltran et al. .. 424/70.27
2004/0204496 A1 10/2004 Ammon, Jr. et al.

FOREIGN PATENT DOCUMENTS

WO 03/034842 5/2003
WO 2008/014824 2/2008

OTHER PUBLICATIONS

Jordan, "Activity of bleach, ethanol and two commercial disinfectants against spores of *Encephalitozoon cuniculi*", Vet Parasitol. Mar. 31, 2006; 136(3-4): 343-6.*
International Search Report and Written Opinion for corresponding PCT/EP2009/058197 mailed Mar. 29, 2011, ten pages.

* cited by examiner

*Primary Examiner* — Sreeni Padmanabhan
*Assistant Examiner* — Sahar Javanmard
(74) *Attorney, Agent, or Firm* — Rankin, Hill & Clark LLP

(57) ABSTRACT

Cationic surfactants derived from the condensation of fatty acids and esterified dibasic amino acids, such as from lauric acid and arginine, in particular the ethyl ester of the lauramide of the arginine monohydrochloride (LAE), may be used for the treatment of objects which are infected with spores. The spores may originate from bacteria or fungi.

11 Claims, No Drawings

USE OF CATIONIC SURFACTANTS AS SPORICIDAL AGENTS

The present application relates to a novel use of cationic surfactants.

Cationic surfactants are known as preservatives used in food, cosmetic and pharmaceutical industry. Cationic surfactants have turned out to be highly effective against microbial proliferation and at the same time safe for intake in humans and mammals in general. For all of this, cationic surfactants are an attractive tool in the industry.

It has been demonstrated that cationic surfactants according to formula (1) derived from the condensation of fatty acids and esterified dibasic amino acids are highly effective protective substances against microorganisms.

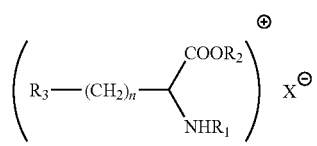

(1)

where:

X⁻ is a counter ion derived from an organic or inorganic acid, preferably Br⁻, Cl⁻ or $HSO_4^-$, or an anion on the basis of a phenolic compound;

$R_1$: is a straight alkyl chain from a saturated fatty acid or hydroxyl acid having from 8 to 14 atoms linked to the α-amino acid group via an amidic bond;

$R_2$: is a straight or branched alkyl chain from 1 to 18 carbon atoms or an aromatic group;

$R_3$: is

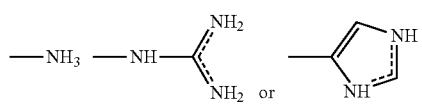

where n is from 0 to 4.

The organic acids which may be the source of the counter ion X⁻ can be citric acid, lactic acid, acetic acid, fumaric acid, maleic acid, gluconic acid, propionic acid, sorbic acid, benzoic acid, carbonic acid, glutamic acid or other amino acids, lauric acid and fatty acids such as oleic acid and linoleic acid, whereas the inorganic acids can be phosphoric acid, nitric acid and thiocyanic acid.

The phenolic compound which may be the basis of the anion X— is for instance butylated hydroxyanisole (BHA) and the related butylated hydroxytoluene, tertiary butyl hydroquinone and parabens such as methylparaben, ethylparaben, propylparaben and butylparaben.

The most preferred compound of the above class of compounds is the ethyl ester of the lauramide of the arginine monohydrochloride, hereafter referred to as LAE (CAS No. 60372-77-2). This compound is now well-known for its use as an antimicrobial agent. In practical use LAE turned out to be well tolerated and to display a very low toxicity to human beings. LAE has the chemical structure of formula (2) displayed hereafter.

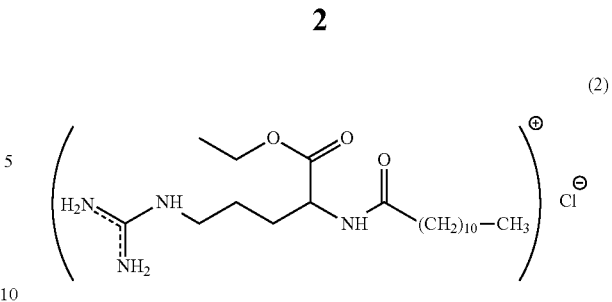

(2)

The compound LAE is remarkable for its activity against different microorganisms, like bacteria, moulds and yeasts which can be present in food products (WO 03/034842) and also in cosmetic formulations and preparations (WO 03/013453, WO 03/013454 and WO 03/043593).

The general preparation of the cationic surfactants is described in Spanish patent ES 512643 and international patent applications WO 96/21642, WO 01/94292 and WO 03/064669.

LAE, also known as lauric arginate, is manufactured by Laboratorios Miret, S.A. (LAMIRSA, Spain). Lauric arginate is listed by the FDA (Food and Drug Administration) as being a GRAS substance (Generally Recognized As Safe) under GRN 000164. The USDA (United States Department of Agriculture) has approved its use in meat and poultry products (FSIS Directive 7120.1)) and also as a processing aid for fresh meat and poultry products.

The metabolism of the above cationic surfactant of formula (2) in rats has been studied; these studies have shown a fast absorption and metabolization into naturally-occurring amino acids and the fatty acid lauric acid, which are eventually excreted as carbon dioxide and urea. Toxicological studies have demonstrated that LAE is completely harmless to animals and humans.

Therefore, LAE and related compounds are particularly suitable to be used in the preservation of all perishable food products. LAE and related compounds are equally suitable for use in cosmetic products.

As has been remarked above, the cationic surfactants are remarkable for their inhibitory action over the proliferation of different microorganisms, such as bacteria, fungi and yeasts. The minimum inhibitory concentrations of LAE are shown in the following table 1.

TABLE 1

| Kind | Microorganism | M.I.C. (ppm) |
|---|---|---|
| Gram + Bacteria | *Arthrobacter oxydans* ATCC 8010 | 64 |
| | *Bacillus cereus* var *mycoide* ATCC 11778 | 32 |
| | *Bacillus subtilis* ATCC 6633 | 16 |
| | *Clostridium perfringens* ATCC 77454 | 16 |
| | *Listeria monocytogenes* ATCC 7644 | 10 |
| | *Staphylococcus aureus* ATCC 6538 | 32 |
| | *Micrococcus luteus* ATCC 9631 | 128 |
| | *Lactobacillus delbrueckii* ssp *lactis* CECT 372 | 16 |
| | *Leuconostoc mesenteroides* CETC 912 | 32 |
| Gram − Bacteria | *Alcaligenes faecalis* ATCC 8750 | 64 |
| | *Bordetella bronchiseptica* ATCC 4617 | 128 |
| | *Citrobacter freundii* ATCC 22636 | 64 |
| | *Enterobacter aerogenes* CECT 689 | 32 |
| | *Escherichia coli* ATCC 8739 | 32 |
| | *Escherichia coli* 0157H7 | 20 |
| | *Klebsiella pneumoniae* var *pneumoniae* CECT 178 | 32 |
| | *Proteus mirabilis* CECT 170 | 32 |
| | *Pseudomonas aeruginosa* ATCC 9027 | 64 |
| | *Salmonella typhimurium* ATCC16028 | 32 |
| | *Serratia marcenses* CECT 274 | 32 |
| | *Mycobacterium phlei* ATCC 41423 | 2 |

TABLE 1-continued

| Kind | Microorganism | M.I.C. (ppm) |
|---|---|---|
| Fungi | *Aspergillus niger* ATCC 14604 | 32 |
| | *Aureobasidium pullulans* ATCC 9348 | 16 |
| | *Gliocadium virens* ATCC 4645 | 32 |
| | *Chaetonium globosum* ATCC 6205 | 16 |
| | *Penicillium chrysogenum* CECT 2802 | 128 |
| | *Penicillium funiculosum* CECT 2914 | 16 |
| Yeast | *Candida albicans* ATCC 10231 | 16 |
| | *Rhodotorula rubra* CECT 1158 | 16 |
| | *Saccharomyces cerevisiae* ATCC 9763 | 32 |

It is preferred to dissolve the compound directly before use in one of the following preferred solvents of food grade: water, ethanol, propylene glycol, isopropyl alcohol, other glycols, mixtures of glycols and mixtures of glycols and water, diacetin, triacetin, glycerol, sorbitol, mannitol and xylitol. If the treatment shall be performed at a specific pH value the use of a corresponding buffer solution may be recommendable. On the other hand the compound can be easily used in its solid form or formulated with solid carriers such as salt, sugar, maltodextrine, hydrocolloids and sorbitol.

For the cationic surfactants of the above formula (1) the antibacterial activity and the biological activity against other microorganisms such as fungi and yeasts is well documented.

Effective treatment of bacterial infection is regularly limited due to the capacity of certain bacteria to produce endospores.

An endospore is a dormant, tough, and non-reproductive structure produced by a small number of bacteria from the Firmicute phylum. The primary function of most endospores is to ensure the survival of a bacterium through periods of environmental stress. They are therefore resistant to ultraviolet and gamma radiation, desiccation, lysozyme, temperature, starvation and chemical disinfectants. Endospores are commonly found in soil and water, where they may survive for long periods of time. They are also found in food, cosmetics and at the surfaces of the equipments. Some bacteria produce exospores or cysts instead.

Endospores are resistant to most agents which would normally kill the vegetative cells they are formed from. Household cleaning products generally have no effect, nor do most alcohols, quaternary compounds and detergents. Alkylating agents however, such as ethylene oxide, are effective against endospores.

Whilst resistant to extreme heat and radiation, endospores can be destroyed by burning or autoclaving. Exposure to extreme heat for a long enough period will generally have some effect, though many endospores can survive hours of boiling or cooking. Prolonged exposure to high energy radiation, such as X-rays and gamma rays, will also kill most endospores.

It is an object of the present invention to provide a further agent for killing endospores.

It has been the surprising result of investigations performed by the present inventors that the cationic surfactants according to the above formula (1) display a sporididal activity. No such sporicidal activity of the cationic preservatives had been described before.

The activity of the cationic surfactants is observed against spores of bacteria and moulds, such as against the endospores of bacteria and moulds.

It has been a further surprising observation made by the present inventors, that the cationic surfactants also display a sporicidal activity against endospores generated by fungi.

This enables a highly active treatment of any object which may be infected with the presence of spores from different sources.

The cationic surfactant which is used in the present invention is derived from the condensation of fatty acids and esterified dibasic amino acids, having the above formula (1), the most preferred species of the cationic surfactants of formula (1) being the ethyl ester of lauric arginate of above formula (2).

The cationic surfactants may be administered most conveniently as a solution in a suitable solvent, but it is also possible to perform the treatment of the object which shall be cleaned through the application of the solid form or the solid formulation.

If the cationic surfactants are applied as a solution, and the object to be cleaned is any product which is intended for consumption by humans or animals, the liquid basis of the solution may be any liquid which is suitable for use in the preparation of food. Such liquids are water, propylene glycol, ethanol, or glycerine. Mixtures of these liquids are possible as well.

Water may refer to tap water, demineralised water, distilled water, or solutions of any suitable salt in water.

Dissolution of the cationic surfactants in aqueous solutions is preferred. As the vehicle for the solution, water, such as tap water or demineralised water, is the most suitable, solutions in brine are also possible.

Addition of further solvents is possible, such as any organic solvent, as long as this further added solvent has no negative effect on later consumption by human consumers. In general, there is no specific advantage in adding further solvents and the administration of a solution in tap water is sufficient for usual purposes.

If the treatment is directed to an object which is not intended directly for consumption by humans or animals, the composition is not subject to the same strict requirements and more aggressive solutions may be chosen. Such objects may be surfaces in an industrial environment which may be contaminated with endospore producing bacteria and moulds.

For the wanted effect on the spores a sufficient concentration of the cationic surfactant of the formula (1) needs to be achieved. It has been observed that such sufficient concentration is achieved when the solution contains the cationic surfactant of the formula (1), more in particular according to the preferred embodiment LAE, in a concentration of 0.001 to 5% by weight. A more preferred concentration is in the range of 0.01 to 2.5% by weight and the most preferable concentration in the range of 0.05 to 0.1% by weight.

Application of the solid form onto a surface should lead to a concentration on the treated surface of the cationic surfactants of the formula (1), more in particular according to the preferred embodiment of LAE, of a level which is sufficient to achieve the wanted biological action at such surfaces. Such a sufficient level of concentration would be expected in the range of 10 to 20,000 ppm, more preferred 200 to 15,000 ppm and even more preferred 500 to 12,000 ppm. These concentrations are given in terms of the concentration of a solution containing the cationic surfactant which is applied to the surfaces to be treated. If surfaces are treated with a solid preparation of the cationic surfactant of formula (1), the amount which is applied shall be such, that the amount of the cationic surfactant of formula (1) is in the range of 0.05 to 200 mg/dm$^2$, preferably an amount of 0.5 to 150 mg/dm$^2$, more preferably an amount of 1 to 100 mg/dm² and most preferably an amount of 5 to 80 mg/dm².

A combination with other products is possible, for example with phosphates, polysorbates, chelating agents, nisine, lysozyme, and other products already recognised as sporicides. For instance the aqueous composition for the sporicidal treatment may contain a suitable amount of sodium tripolyphosphate. Such a suitable amount is between 10 and 10,000 ppm and the preferred range is between 100 and 1,000 ppm. When the combination is with polysorbates, the suitable amount is between 10 and 100,000 ppm, with polysorbate 20 being the preferred polysorbate. When the combination is with nisine, the suitable amount is between 10 and 600 ppm and when the combination is done with lysozyme the suitable amount is on the range from 20 to 400 ppm.

EXAMPLE 1

The determination of the sporicidal activity of LAE has been carried out according to the European standard EN 13704:2002 "Chemical disinfectant—Quantitative suspension test for the evaluation of sporicidal activity of chemical disinfectants used in food, industrial, domestic and institutional areas—Test method and requirements".

The purpose of the example is to demonstrate the activity of LAE on bacterial endospores from the test organism *Bacillus subtilis*.

A test suspension containing endospores from *Bacillus subtilis* ATCC 6633 was prepared from a culture grown on a nutrient agar, to which additional sporulation enhancement ingredients were added. Plates were harvested with sterile water and endospores were purified by repeated centrifugations and resuspensions in water.

Neutralizer. The neutralizer mixture consisted of 12.7% polysorbate 80, 6.0% Tamol® SN (brand of sodium salt of naphthalene-formaldehyde condensate), 1.7% lecithin, 1% peptone and 0.1% cystine. The solution was intended to neutralize any chemicals so that these would not affect subsequent growth of the bacteria.

The sporicidal activity of a given product is defined by its capacity to reduce at least by $10^3$ the amount of *Bacillus subtilis* bacterial spores in suspension, in the conditions established in the method.

LAE is produced by Lamirsa.

The product was in contact with a suspension of bacterial spores during an established period of time of 60 minutes. An interfering substance can be added to the suspension, in this case 0.3% bovine serum albumin in distilled water. Next, the effect of the product is neutralized by adding a neutralizer previously chosen, preceding to the surviving spores count.

Procedure:
1. Spore suspension obtained from a spored-form culture of *Bacillus subtilis*.
2. Count of the spore suspension of *Bacillus subtilis*.
3. The possible toxic effect of the neutralizer on the spores in the absence of the product is valued.
4. Evaluation of the neutralizing effect of the neutralizer over the product.
4. Evaluation of the inhibitory effect of the product.
5. Result calculation.

Results:
Results are expressed as the reduction of viability of the spore suspension in regards to:
 Validation of the neutralization of the product,
 Validation of the non toxicity of the neutralizer,
 Sporicidal activity of the product.
Tabulation of the Method and Test Validation Results (at 20° C.):

| | | |
|---|---|---|
| Mother spore suspension | | $1.5 \times 10^9$ cfu/mL |
| Method validation, control | | $1.2 \times 10^6$ cfu/mL |
| Neutralizer toxicity | | $1.8 \times 10^3$ cfu/mL |
| Neutralizer control | | $1.8 \times 10^3$ cfu/mL |
| Test spore suspension (N) | | $3.8 \times 10^3$ cfu/mL validation tests |
| | | $1.8 \times 10^7$ cfu/mL product tests |
| Test of LAE sporicidal activity (µg/mL) ($N_a$) | 12.5 µg/mL | >300 cfu/mL (countless) |
| | 25 µg/mL | >300 cfu/mL (countless) |
| | 50 µg/mL | $5.2 \times 10^3$ cfu/mL |
| | 100 µg/mL | $5.3 \times 10^3$ cfu/mL |
| | 150 µg/mL | $4.2 \times 10^3$ cfu/mL |
| | 250 µg/mL | No cfu/mL |
| | 300 µg/mL | No cfu/mL | cfu: colony forming unit

The results drawn from the validation test indicate, that the used neutralizer (Polysorbate 80 in water solution at 2%) is not toxic and neutralizes the effect of the product, because in both cases the viable spore count is similar to the used solution in the respective tests.

The sporicidal activity is calculated as follows:

$$R = N \times 0.1/N_a$$

N is cfu/mL of the spore suspension.
$N_a$ is cfu/mL of the sporicidal activity.
The calculated reduction of a solution of:
 50 ppm of LAE is $R = 3.5 \times 10^2$ cfu/mL
 100 ppm of LAE is $R = 3.4 \times 10^2$ cfu/mL
 150 ppm of LAE is $R = 4.3 \times 10^2$ cfu/mL
 250 ppm of LAE is $R > 10^3$ cfu/mL The data show, that from a LAE concentration of 50 ppm there is inhibition of spore germination.

A product is considered sporicidal if its use results in a reduction in the number of *Bacillus subtilis* bacterial spores equal or above $10^3$ after being in contact for 60 minutes in the conditions set in EN 13704:2000.

Therefore, LAE displays a sporicidal activity against endospores of *Bacillus subtilis* at concentrations equal to or above 250 ppm. The species is the usual species in testing of sporicidal activity. The species belongs to the same genus as the bacterial organism which causes anthrax. Due to their genetic similarities, *B. subtilis* spores have been used as a non-pathogenetic replacement for spores of *Bacillus anthracis*, the anthrax bacterium. The present results are expected to be applicable to anthrax.

EXAMPLE 2

The determination of the fungicide activity of LAE has been carried out according to the European standard UNE-EN 1275: "Chemical disinfectant and antiseptic. Fungicide activity. Test method and requirements".

The fungicide activity of a given product is defined by its capacity to reduce at least by $10^4$ the amount of *Aspergillus niger* fungical spores in suspension, in the conditions established in the method.

LAE is produced by Lamirsa.

The product is in contact with a suspension of fungical spores during an established period of time (60 minutes). After this time, the effect of the product is neutralized by adding Polysorbate 80 in water solution at 2%, preceding to the surviving spores count.

Procedure:
1. Spore suspension obtained from a spored-form culture of *Aspergillus niger*.
2. Count of the spore suspension of *Aspergillus niger*.
3. The possible toxic effect of the neutralizer on the spores in the absence of the product is valued.
4. Evaluation of the neutralizing effect of the neutralizer over the product.
5. Evaluation of the fungicide effect of the product.
6. Result calculation.

Results:

Results are expressed as the reduction of viability of the spore suspension in regards to:
- Validation of the neutralization of the product,
- Validation of the non toxicity of the neutralizer,
- Fungicide activity of the product.

Tabulation of the Method and Test Validation Results (at 20° C.):

| | | |
|---|---|---|
| Mother spore suspension | | $1.8 \times 10^9$ cfu/mL |
| Method validation, control | | $3.5 \times 10^7$ cfu/mL |
| Neutralizer toxicity | | $3.8 \times 10^3$ cfu/mL |
| Neutralizer control | | $2.7 \times 10^3$ cfu/mL |
| Test spore suspension (N) | | $4 \times 10^3$ cfu/mL validation test |
| | | $5 \times 10^7$ cfu/mL product test |
| Test of LAE fungicide activity (μg/mL) ($N_a$) | 12.5 μg/mL | >300 cfu/mL (countless) |
| | 25 μg/mL | >300 cfu/mL (countless) |
| | 50 μg/mL | >300 cfu/mL (countless) |
| | 100 μg/mL | $1.6 \times 10^4$ cfu/mL |
| | 200 μg/mL | $3.9 \times 10^3$ cfu/mL |
| | 300 μg/mL | $3.5 \times 10^3$ cfu/mL |
| | 400 μg/mL | $3.0 \times 10^3$ cfu/mL |
| | 500 μg/mL | No cfu/mL |
| | 1000 μg/mL | No cfu/mL | cfu: colony forming unit

Fungicide activity is calculated as follows:

$$R = N \times 0.1/N_a$$

N cfu/mL of the fungical spore suspension
$N_a$ cfu/mL of the fungicide activity The calculated reduction of a solution of:
- 100 μg/mL of LAE is $R = 3.1 \times 10^2$ cfu/mL
- 200 μg/mL of LAE is $R = 1.3 \times 10^3$ cfu/mL
- 300 μg/mL of LAE is $R = 1.4 \times 10^3$ cfu/mL
- 400 μg/mL of LAE is $R = 1.7 \times 10^3$ cfu/mL
- 500 μg/mL of LAE is $R > 10^4$ cfu/mL As seen, from 100 ppm there is inhibition of fungical spore germination.

From 500 ppm, a total inhibition of fungical spore germination has been observed.

A product is considered fungicide if its use results in a reduction in the number of *Aspergillus niger* fungical spores equal to or above $10^4$ after being in contact for 60 minutes in the conditions set in UNE-EN 1275.

Therefore, LAE is fungicide active at concentrations equal to or above 500 ppm.

EXAMPLE 3

The determination of the sporicidal activity of LAE has been carried out according to the European standard EN 13704:2002: "Chemical disinfectant—Quantitative suspension test for the evaluation of sporicidal activity of chemical disinfectants used in food, industrial, domestic and institutional areas—Test method and requirements".

The purpose of the example is to demonstrate the activity of LAE on bacterial endospores from the test organism *Geobacillus stearothermophilus*.

A test suspension containing endospores from *Geobacillus stearothermophilus* ATCC 12980 was prepared from a culture grown on a nutrient agar, to which additional sporulation enhancement ingredients were added. Plates were harvested with sterile water and endospores were purified by repeated centrifugations and resuspensions in water.

Neutralizer. The neutralizer mixture consisted of 30 g/L polysorbate 80 in water. The solution was intended to neutralize any chemicals so that these would not affect subsequent growth of the bacteria.

The sporicidal activity of a given product is defined by its capacity to reduce at least by $10^3$ the amount of *Geobacillus stearothermophilus* bacterial spores in suspension, in the conditions established in the method.

LAE is produced by Lamirsa.

The product was in contact with a suspension of bacterial spores during an established period of time of 60 minutes. An interfering substance can be added to the suspension, in this case water. Next, the effect of the product is neutralized by adding a neutralizer previously chosen, preceding to the surviving spores count.

Procedure:
1. Spore suspension obtained from a spored-form culture of *Geobacillus stearothermophilus*
2. Count of the spore suspension of *Geobacillus stearothermophilus*.
3. The possible toxic effect of the neutralizer on the spores in the absence of the product is valued.
4. Validation of the dilution-neutralisation method.
5. Evaluation of the inhibitory sporicide effect of the product.
6. Result calculation.

Results:
Results are expressed as the reduction of viability of the spore suspension in regards to:
  Validation of the neutralization of the product,
  Validation of the non toxicity of the neutralizer,
  Sporicidal activity of the product.
Tabulation of the Method and Test Validation Results (at 40° C.):

| | | |
|---|---|---|
| Mother spore suspension | 2.8 × 10$^8$ cfu/mL | |
| Method validation, control | 1.3 × 10$^4$ cfu/mL | |
| Neutralizer toxicity | 1.1 × 10$^4$ cfu/mL | |
| Neutralizer control | 1.2 × 10$^4$ cfu/mL | |
| Test spore suspension (N) | 1.6 × 10$^4$ cfu/mL validation test | |
| | 1.3 × 10$^6$ cfu/mL product test | |
| Test of LAE sporicidal activity (μg/mL) (N$_a$) | 58 μg/mL | 1.0 × 10$^5$ cfu/mL |
| | 115 μg/mL | 5.2 × 10$^4$ cfu/mL |
| | 173 μg/mL | <10$^2$ cfu/mL |
| | 230 μg/mL | <10$^2$ cfu/mL |
| | 460 μg/mL | <10$^2$ cfu/mL | cfu: colony forming unit

The results drawn from the validation test indicate that the used neutralizer (30 g/L polysorbate 80 in water) is not toxic and neutralizes the effect of the product because in both cases the viable spore count is similar to the used solution in the respective tests.

Sporicidal activity is calculated following the criteria of the Standard EN 13704: 2002

$$R = N \times 0.1/N_a$$

N is cfu/mL of the spore suspension
N$_a$ is cfu/mL of the sporicidal activity
The calculated reduction (R) at different concentration of LAE against *G. stearothermophilus* is:
  58 μg/ml of LAE is R<10$^3$ cfu/mL
  115 μg/ml of LAE is R<10$^3$ cfu/mL
  173 μg/ml of LAE is R>10$^3$ cfu/mL
  230 μg/ml of LAE is R>10$^3$ cfu/mL
  460 μg/ml of LAE is R>10$^3$ cfu/mL A product is considered sporicidal, if its use results in a reduction (R) in the number of *Geobacillus stearothermophilus* bacterial spores equal to or above 10$^3$ after being in contact for 60 minutes in the conditions set in EN 13704:2002.

Therefore, LAE displays a sporicidal activity against endospores of *Geobacillus stearothermophilus* at concentrations equal to or above 173 μg/ml.

EXAMPLE 4

The determination of the sporicidal activity of LAE has been carried out according to the European standard EN 13704:2002: "Chemical disinfectant—Quantitative suspension test for the evaluation of sporicidal activity of chemical disinfectants used in food, industrial, domestic and institutional areas—Test method and requirements".

The purpose of the example is to demonstrate the activity of LAE on bacterial endospores from the test organism *Thermoanaerobacterium thermosaccharolyticum*.

A test suspension containing endospores from *Thermoanaerobacterium thermosaccharolyticum* ATCC 7956 was prepared from a culture grown on a nutrient agar, to which additional sporulation enhancement ingredients were added. Plates were harvested with sterile water and endospores were purified by repeated centrifugations and resuspensions in water.

Neutralizer. The neutralizer mixture consisted of 30 g/L polysorbate 80 in water. The solution was intended to neutralize any chemicals so that these would not affect subsequent growth of the bacteria.

The sporicidal activity of a given product is defined by its capacity to reduce at least by 10$^3$ the amount of *Thermoanaerobacterium thermosaccharolyticum* bacterial spores in suspension, in the conditions established in the method.

LAE is produced by Lamirsa.

The product was in contact with a suspension of bacterial spores during an established period of time of 60 minutes. An interfering substance can be added to the suspension, in this case water. Next, the effect of the product is neutralized by adding a neutralizer previously chosen, preceding to the surviving spores count.

Procedure:
1. Spore suspension obtained from a spored-form culture of *Thermoanaerobacterium thermosaccharolyticum*.
2. Count of the spore suspension of *Thermoanaerobacterium thermosaccharolyticum*.
3. The possible toxic effect of the neutralizer on the spores in the absence of the product is valued.
4. Validation of the dilution-neutralisation method.
5. Evaluation of the inhibitory sporicide effect of the product.
6. Result calculation.

Results:
Results are expressed as the reduction of viability of the spore suspension in regards to:
  Validation of the neutralization of the product,
  Validation of the non toxicity of the neutralizer,
  Sporicidal activity of the product.
Tabulation of the Method and Test Validation Results (at 20° C.):

| | | |
|---|---|---|
| Mother spore suspension | 1.0 × 10$^6$ cfu/mL | |
| Method validation, control | 4 × 10$^3$ cfu/mL | |
| Neutralizer toxicity | 5 × 10$^3$ cfu/mL | |
| Neutralizer control | 3 × 10$^3$ cfu/mL | |
| Test spore suspension (N) | 5 × 10$^3$ cfu/mL validation test | |
| | 0.65 × 10$^6$ cfu/mL product test | |
| Test of LAE sporicidal activity (μg/mL) (N$_a$) | 32 μg/mL | 2.7 × 10$^3$ cfu/mL |
| | 51 μg/mL | 1.6 × 10$^3$ cfu/mL |
| | 102 μg/mL | <10$^2$ cfu/mL |
| | 205 μg/mL | <10$^2$ cfu/mL | cfu: colony forming unit

The results drawn from the validation test indicate that the used neutralizer (30 g/L polysorbate 80 in water) is not toxic and neutralizes the effect of the product because in both cases the viable spore count is similar to the used solution in the respective tests.

Sporicidal activity is calculated following the criteria of the Standard EN 13704:2002:

$$R = N \times 0.1/N_a$$

N is cfu/mL of the spore suspension
N$_a$ is cfu/mL of the sporicidal activity
The calculated reduction of a solution of:
  32 μg/mL of LAE is R<10$^3$ cfu/mL
  51 μg/mL of LAE is R<10$^3$ cfu/mL
  102 μg/mL of LAE is R>10$^3$ cfu/mL
  205 μg/mL of LAE is R>10$^3$ cfu/mL A product is considered sporicidal if its use results in a reduction (R) in the number of *Thermoanaerobacterium thermosaccharolyticum* bacterial spores equal to or above 10$^3$ after being in contact for 60 minutes in the conditions set in EN 13704:2002.

Therefore, LAE displays a sporicidal activity against endospores on *Thermoanaerobacterium thermosaccharolyticum* in concentrations equal or above 102 µg/mL.

EXAMPLE 5

The determination of the sporicidal activity of LAE has been carried out according to the European standard EN 13704:2002 Chemical disinfectant—Quantitative suspension test for the evaluation of sporicidal activity of chemical disinfectants used in food, industrial, domestic and institutional areas—Test method and requirements".

The purpose of the example is to demonstrate the activity of LAE on bacterial endospores from the test organism *Clostridium sporogenes*.

A test suspension containing endospores from *Clostridium sporogenes* ATCC 7955 was prepared from a culture grown on a nutrient agar, to which additional sporulation enhancement ingredients were added. Plates were harvested with sterile water and endospores were purified by repeated centrifugations and resuspensions in water.

Neutralizer. The neutralizer mixture consisted of 30 g/L polysorbate 80 in water. The solution was intended to neutralize any chemicals so that these would not affect subsequent growth of the bacteria.

The sporicidal activity of a given product is defined by its capacity to reduce at least by $10^3$ the amount of *Clostridium sporogenes* bacterial spores in suspension, in the conditions established in the method.

LAE is produced by Lamirsa.

The product was in contact with a suspension of bacterial spores during an established period of time of 60 minutes. An interfering substance can be added to the suspension, in this case water. Next, the effect of the product is neutralized by adding a neutralizer previously chosen, preceding to the surviving spores count.

Procedure:
1. Spore suspension obtained from a spored-form culture of *Clostridium sporogenes*.
2. Count of the spore suspension of *Clostridium sporogenes*.
3. The possible toxic effect of the neutralizer on the spores in the absence of the product is valued.
4. Validation of the dilution-neutralisation method.
5. Evaluation of the inhibitory sporicide effect of the product.
6. Result calculation.

Results:
Results are expressed as the reduction of viability of the spore suspension in regards to:
   Validation of the neutralization of the product,
   Validation of the non toxicity of the neutralizer,
   Sporicidal activity of the product.

Tabulation of the Method and Test Validation Results (at 20° C.):

| | |
|---|---|
| Mother spore suspension | $1.3 \times 10^6$ cfu/mL |
| Method validation, control | $1.3 \times 10^3$ cfu/mL |
| Neutralizer toxicity | $5 \times 10^3$ cfu/mL |
| Neutralizer control | $6 \times 10^3$ cfu/mL |
| Test spore suspension (N) | $8 \times 10^3$ cfu/mL validation test |
| | $1.3 \times 10^6$ cfu/mL product test |

-continued

| | | |
|---|---|---|
| Test of LAE sporicidal activity (µg/mL) ($N_a$) | 13 µg/mL | $3.3 \times 10^3$ cfu/mL |
| | 26 µg/mL | $2.3 \times 10^3$ cfu/mL |
| | 51 µg/mL | $<10^2$ cfu/mL |
| | 64 µg/mL | $<10^2$ cfu/mL | cfu: colony forming unit

The results drawn from the validation test indicate that the used neutralizer (30 g/L polysorbate 80 in water) is not toxic and neutralizes the effect of the product because in both cases the viable spore count is similar to the used solution in the respective tests.

Sporicidal activity is calculated following the criteria of the Standard EN 13704: 2002

$$R = N \times 0.1/N_a$$

N is cfu/mL of the spore suspension.
$N_a$ is cfu/mL of the sporicidal activity.
The calculated reduction (R) of a solution of:
   13 µg/mL of LAE is R<$10^3$ cfu/mL
   26 µg/mL of LAE is R<$10^3$ cfu/mL
   51 µg/mL of LAE is R>$10^3$ cfu/mL
   64 µg/mL of LAE is R>$10^3$ cfu/mL A product is considered sporicidal if its use results in a reduction in the number of *Clostridium sporogenes* bacterial spores equal or above $10^3$ after being in contact for 60 minutes in the conditions set in EN 13704:2002.

Therefore, LAE displays a sporicidal activity against endospores on *Clostridium sporogenes* in concentrations equal or above 51 µg/mL.

EXAMPLE 6

The determination of the sporicidal activity of a combination of LAE with sodium tripolyphosphate has been carried out according to the European standard EN 13704:2002: "Chemical disinfectant—Quantitative suspension test for the evaluation of sporicidal activity of chemical disinfectants used in food, industrial, domestic and institutional areas—Test method and requirements".

The purpose of the example is to demonstrate the activity of the combination of LAE and sodium tripolyphosphate on bacterial endospores from the test organism *Geobacillus stearothermophilus*.

A test suspension containing endospores from *Geobacillus stearothermophilus* ATCC 12980 was prepared from a culture grown on a nutrient agar, to which additional sporulation enhancement ingredients were added. Plates were harvested with sterile water and endospores were purified by repeated centrifugations and resuspensions in water.

Neutralizer. The neutralizer mixture consisted of 30 g/L polysorbate 80 in water. The solution was intended to neutralize any chemicals so that these would not affect subsequent growth of the bacteria.

The sporicidal activity of a given product is defined by its capacity to reduce at least by $10^3$ the amount of *Geobacillus stearothermophilus* bacterial spores in suspension, in the conditions established in the method.

LAE is produced by Lamirsa.

The following solutions were tested:
   (1) a solution of LAE (1%) and polysorbate 20 (7.5%);
   (2) a solution of sodium tripolyphosphate (5%) and polysorbate 20 (10%);

(3) a solution containing LAE (1%), sodium tripolyphosphate (0.2%), polysorbate 20 (7.5%) and sodium chloride (0.4%);

(4) a solution containing LAE (1%), sodium tripolyphosphate (5.0%) and polysorbate 20 (7.5%).

The products were in contact with a suspension of bacterial spores during an established period of time of 60 minutes. An interfering substance can be added to the suspension; in this case, 0.3% bovine serum albumin in distilled water. Next, the effect of the product is neutralized by adding a neutralizer previously chosen, preceding to the surviving spores count.

Procedure:

1. Spore suspension obtained from a spored-form culture of *Geobacillus stearothermophilus*.
2. Count of the spore suspension of *Geobacillus stearothermophilus*.
3. The possible toxic effect of the neutralizer on the spores in the absence of the product is valued.
4. Validation of the dilution-neutralisation method.
5. Evaluation of the inhibitory sporicide effect of the product.
6. Result calculation.

Results:

Results are expressed as the reduction of viability of the spore suspension in regards to:

Validation of the neutralization of the product,

Validation of the non toxicity of the neutralizer,

Sporicidal activity of the product.

Tabulation of the Method and Test Validation Results (at 20° C.):

| | |
|---|---|
| Stock spore suspension | $1.8 \times 10^8$ cfu/mL |
| Experimental conditions validation (A) | $1.3 \times 10^3$ cfu/mL |
| Neutralizer toxicity validation (B) | $1.1 \times 10^4$ cfu/mL |
| Dilution-neutralizing validation (C) 64 µg/mL LAE | $1.4 \times 10^3$ cfu/mL |
| Validation assay on the spore suspension ($N_v$) | $1.8 \times 10^3$ cfu/mL validation test |
| Product assay on the spore suspension (N) | $1.8 \times 10^6$ cfu/mL product test |
| Sporicidal activity of F.1 (mg/mL) ($N_a$) | 255 mg/mL $<10^2$ cfu/mL |
| | 25.5 mg/mL $1.7 \times 10^2$ cfu/mL |
| | 12.75 mg/mL $8.9 \times 10^2$ cfu/mL |
| | 6.37 mg/mL $>10^2$ cfu/mL |
| | 3.18 mg/mL $>10^2$ cfu/mL |
| Sporicidal activity of F.2 (mg/mL) ($N_a$) | 51.2 mg/ml $<10^2$ cfu/mL |
| | 5.12 mg/ml $1 \times 10^1$ cfu/mL |
| | 2.56 mg/ml $1.5 \times 10^1$ cfu/mL |
| | 1.27 mg/ml $>10^2$ cfu/mL |
| | 0.64 mg/ml $>10^2$ cfu/mL |
| Sporicidal activity of F.3 (mg/mL) ($N_a$) | 255 mg/mL $<10^2$ cfu/mL |
| | 25.5 mg/mL $<10^2$ cfu/mL |
| | 12.75 mg/mL $1.0 \times 10^2$ cfu/mL |
| | 6.37 mg/mL $1.0 \times 10^2$ cfu/mL |
| | 3.18 mg/mL $5.9 \times 10^2$ cfu/mL |
| Sporicidal activity of F.4 (mg/mL) ($N_a$) | 51.2 mg/ml $<10^2$ cfu/mL |
| | 5.12 mg/ml $<10^2$ cfu/mL |
| | 2.56 mg/ml $7 \times 10^1$ cfu/mL |
| | 1.27 mg/ml $3.5 \times 10^2$ cfu/mL |
| | 0.64 mg/ml $3.4 \times 10^2$ cfu/mL | cfu: colony forming unit

The results drawn from the validation test indicate that the used neutralizer (30 g/L polysorbate 80 in water) is not toxic and neutralizes the effect of the product because in both cases the viable spore count is similar to the used solution in the respective tests.

Following the criteria of the Standard EN 13704:2002, the sporicidal activity is calculated using the following expression:

$$R = N \times 0.1/N_a$$

N is cfu/mL number of the spore test suspension.

$N_a$ is cfu/mL number of spore test after the test for sporicidal activity of the product.

The reduction in viability found for the products tested at different concentration against *G. stearothermophilus* were:

| F.1 (AG-024) (mg/mL) | LAE content (µg/mL) | Reduction (R) (cfu./mL) |
|---|---|---|
| 255 | 2040 | $R > 10^3$ |
| 25.5 | 204 | $R = 10^3$ |
| 12.75 | 102 | $R < 10^3$ |
| 6.37 | 51 | $R < 10^3$ |
| 3.18 | 25.5 | $R < 10^3$ |

| F.2 (AG-024) (mg/mL) | TPP content (µg/mL) | Reduction (R) (cfu./mL) |
|---|---|---|
| 51.2 | 2048 | $R > 10^3$ |
| 5.12 | 205 | $R > 10^3$ |
| 2.56 | 102 | $R = 10^3$ |
| 1.27 | 51 | $R < 10^3$ |
| 0.64 | 26 | $R < 10^3$ |

| F.3 (AG-024) (mg/mL) | LAE content (µg/mL) | TPP content (µg/mL) | Reduction (R) (cfu./mL) |
|---|---|---|---|
| 255 | 2040 | 408 | $R > 10^3$ |
| 25.5 | 204 | 41 | $R > 10^3$ |
| 12.75 | 102 | 20 | $R > 10^3$ |
| 6.37 | 51 | 10 | $R > 10^3$ |
| 3.18 | 26 | 5 | $R < 10^3$ |

| F.4 (AG-024) (mg/mL) | LAE content (µg/mL) | TPP content (µg/mL) | Reduction (R) (cfu./mL) |
|---|---|---|---|
| 51.20 | 4090 | 2048 | $R > 10^3$ |
| 5.12 | 41 | 205 | $R > 10^3$ |
| 2.56 | 20 | 102 | $R > 10^3$ |
| 1.27 | 10 | 51 | $R < 10^3$ |
| 0.64 | 5 | 26 | $R < 10^3$ |

TPP: Sodium tripolyphosphate.

According to Standard EN 13704:2002, the sporicidal activity of the product for *Geobacillus stearothermophilus* ATCC 12980 is assessed when at least a reduction of $10^3$ cfu/mL is found.

F.1 at a concentration of 25.5 mg/mL after 1 hour of contact at 20° C. has sporicidal activity. That is 204 µg/ml of LAE F.2 at a concentration of 2.56 mg/mL after 1 hour of contact at 20° C. has sporicidal activity. That is 102 µg/ml of tripolyphosphate F.3 at a concentration of 6.37 mg/mL after 1 hour of contact at 20° C. has sporicidal activity. That is 51 µg/ml of LAE F.4 at a concentration of 2.56 mg/mL after 1 hour of contact at 20° C. has sporicidal activity. That is 20 µg/ml of LAE

The invention claimed is:
1. A method of killing spores comprising
(a) applying to an object infected with spores, a composition including a cationic surfactant derived from the condensation of fatty acids and esterified dibasic amino acids, the cationic surfactant having the following formula:

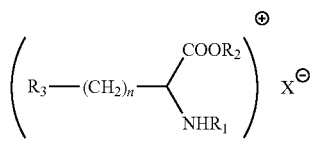

where:
X⁻ is Br⁻, Cl⁻, or HSO₄⁻, a counter ion derived from an organic or inorganic acids, or an anion derived from a phenolic compound;
R₁: is a linear alkyl chain from a saturated fatty acid or hydroxyacid from 8 to 14 atoms of carbon bonded to the α-amino acid group through an amidic bond,
R₂: is a linear or branched alkyl chain from 1 to 18 carbon atoms or an aromatic group,
R₃: is

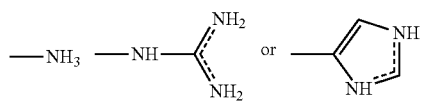

and n can be from 0 to 4, wherein the spores come from at least one of microorganisms, bacteria, fungi, yeasts and molds.

2. The method of claim 1, wherein cationic surfactant is the ethyl ester of the lauramide of arginine monohydrochloride (LAE) of formula (2)

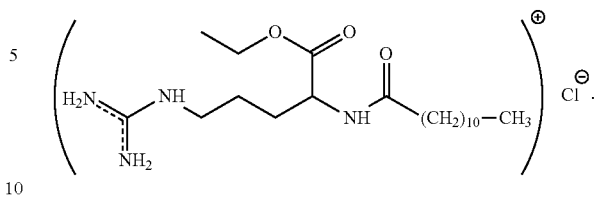

3. The method of claim 1, wherein the spores originate from bacteria.
4. The method of claim 1, wherein the spores originate from fungi.
5. The method of claim 1, wherein the composition comprising the cationic surfactant further comprises a solvent selected from the group consisting of water, propylene glycol, ethanol, glycerin and combinations thereof.
6. The method of claim 1, wherein the composition comprising the cationic surfactant further comprises at least one selected from the group consisting of preservatives, antioxidants, surfactants, thickeners, enzymatic inhibitors, organic and inorganic salts, organic and inorganic acids and liquid and solid carriers.
7. The method of claim 1, wherein the concentration of the cationic surfactant in the composition including the cationic surfactant is in the range of 0.0001 to 5% by weight.
8. The method of claim 1, wherein the composition comprising the cationic surfactant further comprises polysorbates at a dose level range between 10 and 100,000 ppm.
9. The method of claim 1, wherein the cationic surfactant is combined with a further sporicidal agent.
10. The method of claim 9, wherein the further sporicidal agent is sodium tripolyphosphate at a dose level range between 10 and 10,000 ppm.
11. The method of claim 1, wherein the object is selected from the group consisting of food, cosmetics and equipment surfaces.

* * * * *